US00PP26791P3

(12) United States Plant Patent
Radler

(10) Patent No.: US PP26,791 P3
(45) Date of Patent: Jun. 7, 2016

(54) SHRUB ROSE PLANT NAMED 'RADSOUTHTHREE'

(50) Latin Name: *Rosa hybrida*
Varietal Denomination: cv. Radsouththerе

(71) Applicant: CP DELAWARE, INC., Wilmington, DE (US)

(72) Inventor: William J. Radler, Greenfield, WI (US)

(73) Assignee: CP DELAWARE, INC., Wilmington, DE (US)

( * ) Notice: Subject to any disclaimer, the term of this patent is extended or adjusted under 35 U.S.C. 154(b) by 204 days.

(21) Appl. No.: 13/999,450

(22) Filed: Feb. 27, 2014

(65) Prior Publication Data

US 2015/0245550 P1 Aug. 27, 2015

(51) Int. Cl.
*A01H 5/02* (2006.01)

(52) U.S. Cl.
USPC ..... Plt./107

(58) Field of Classification Search
USPC ..... Plt./101, 102, 107
See application file for complete search history.

(56) References Cited

PUBLICATIONS

"HelpMeFind" website for roses, clematis and peonies. Cultivar 'Radsouththerе' Retrieved from the Internet https://www.helpmefind.com/gardening/l.php?l=2.71492.1 (1 page total).*

* cited by examiner

*Primary Examiner* — Susan McCormick Ewoldt
*Assistant Examiner* — Karen Redden
(74) *Attorney, Agent, or Firm* — Buchanan Ingersoll & Rooney PC

(57) ABSTRACT

A new and distinct shrub rose plant is provided that abundantly forms attractive single dark pink blossoms that finish to a coral red coloration. The plant exhibits vigorous vegetation and a compact and bushy growth habit. The foliage is dark green with a glossy upper surface. The dark pink blossom coloration contrasts nicely with the dark green foliage. The disease resistance is excellent, particularly with respect to black spot, rust, and mildews. The plant is well suited for providing attractive ornamentation in in the landscape.

1 Drawing Sheet

Botanical/commercial classification: *Rosa hybrida*/Shrub Rose Plant.

Varietal denomination: cv. Radsouththerе.

SUMMARY OF THE INVENTION

The new variety of *Rosa hybrida* landscape shrub rose plant of the present invention was created at Greenfield, Wis., U.S.A. The seed that produced the new variety of landscape shrub rose was obtained by the cross of unreleased and unnamed breeding plants (each non-patented in the United States) of unknown origin. No further definitive information concerning the identity of the parents is available.

The seeds resulting from the above pollination were sown and small plants were obtained which were physically and biologically different from each other. Selective study resulted in the identification of a single plant of the new variety.

It was found that the new Landscape Shrub rose plant of the present invention possesses the following combination of characteristics:

(a) abundantly forms attractive single dark pink blossoms having yellow centers that finish to a coral red coloration,
(b) exhibits a compact and bushy growth habit,
(c) forms vigorous vegetation,
(d) forms attractive dark green foliage that is glossy on the upper surface and contrasts well with the blossom coloration, (e) exhibits excellent disease resistance particularly with respect to black spot, rust, and mildews, and
(f) is well suited for growing as attractive ornamentation in the landscape.

A new rose variety is provided having attractive single dark pink blossoms with yellow centers that finish to a coral red coloration combined with substantially continuous blooming, a compact growth habit, and excellent disease resistance.

The new variety well meets the needs of the horticultural industry. It can be grown to advantage as ornamentation in parks, gardens, public areas, and in residential settings. Accordingly, the plant is particularly well suited for growing in the landscape. The dark pink flower coloration combined with the glossy dark green foliage is particularly attractive.

The new variety of the present invention can be readily distinguished from other shrub rose plants including the 'Sprothrive' variety (U.S. Plant Pat. No. 23,549) through an inspection of the blossoms. For instance, the single blossoms of dark pink coloration of the new variety are dissimilar to the dark red blossoms of the 'Sprothrive' variety.

The characteristics of the new variety have been found at Wasco, Calif., U.S.A., to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radsouththerе', and will be marketed under the FRUIT PUNCH trademark.

BRIEF DESCRIPTION OF THE PHOTOGRAPH

The accompanying photograph shows, as nearly true as it is reasonably possible to make the same in a color illustration of this character, typical blossoms and foliage of the new variety. The illustrated rose plants of the new variety were approximately two years of age and were observed during May while growing outdoors on their own roots at West Grove, Pa., U.S.A.

DETAILED BOTANICAL DESCRIPTION

The chart used in the identification of colors is that of The Royal Horticultural Society (R.H.S. Colour Chart—1995 Edition or equivalent), London, England. The description is based on the observation of two-year-old specimens of the new variety during October while growing outdoors on their own roots at West Grove, Pa., U.S.A.

Class: Landscape Shrub Rose. Cultivar Radsouththree.

Plant:

*Height*.—Approximately 3 feet on average, and commonly approximately 3 feet on average at full maturity.

*Width*.—Approximately 60 cm on average, and commonly approximately 90 to 120 cm on average at full maturity.

*Habit*.—Compact and bushy.

Branches:

*Color*.—Near Green Group 138A on young stems, and commonly near Green Group 137C commonly with some patches of rough wood that are near Grey-Brown Group 199A.

*Thorns*.—Size: when young commonly approximately 6 mm in length and approximately 4 mm in width at the widest point, and when mature commonly approximately 1 cm in length, and approximately 5 mm in width at the widest point. Color: commonly near Red-Purple Group 58A when young, and near Greyed-Green Group 197C when mature.

Leaves:

*Size*.—Commonly approximately 8.5 cm in length on average and approximately 7.5 cm in width on average for a five-leaflet leaf.

*Leaflets*.—Number: 3, 5, and 7. Length: lower leaflet length is approximately 3.3 cm on average; terminal leaflet length is approximately 5 cm on average when there are 3 leaflets, approximately 4.5 cm on average when there are 5 leaflets, and approximately 3.5 cm on average when there are 7 leaflets. Width: approximately 3 cm on average for a terminal leaflet, and approximately 2.3 cm on average for a lower leaflet. Shape: ovate. Margins: serrate. Texture: generally smooth on the upper and under surfaces. Overall appearance: attractive dark green leaves with a glossy upper surface. Color: (when young): Upper surface: near Green Group 137C commonly with a margin of Red-Purple Group 60A. Under surface: near Yellow-Green Group 146C. Color (when fully mature): Upper surface: near Green Group 139A. Under surface: near Green Group 137B.

*Rachis*.—Color: near Green Group 137C overlaid with Red-Purple Group 60A. Texture: smooth and covered in a small amount of flexible thorns measuring less than 2 mm in length on average.

*Petiole*.—Color: near Green Group 137C overlaid with Red-Purple Group 60A. Texture: smooth.

Inflorescence:

*Number of flowers*.—Commonly one per stem or approximately 3 to 10 blooms in a cluster.

*Peduncle*.—Near Green Group 138A in coloration, commonly approximately 3.5 cm in length on average, approximately 2 mm in diameter on average, smooth in texture, and commonly covered with small flexible thorns less than 1 mm in length.

*Sepals*.—Upper surface: covered with short pubescence, and commonly near Green Group 138B in coloration. Under surface: commonly somewhat rough in texture, and commonly near Green Group 143C in coloration. Size: commonly approximately 3 cm in length on average, and approximately 8 mm in width at the base. Extensions: commonly with three extensions per sepal measuring approximately 5 mm in length. Number five.

*Buds*.—Shape: generally ovoid. Length: approximately 2.5 mm on average as the calyx breaks. diameter: approximately 1.8 cm on average as the calyx breaks. Color: when opening commonly near Yellow-Group 13A transitioning to Orange-Red Group 34B towards the base.

*Flower*.—Form: single, cuplike. Diameter: commonly approximately 8 cm on average when fully open. Color (when opening): Upper surface: near Yellow Group 12A at the point of attachment, transitioning to Orange-Red Group 31B, and finally near Red Group 46C towards the apex. Under surface: near Yellow Group 3B at the point of attachment blending to Red Group 51B towards the apex. Color (at end of blooming): Upper surface: near Yellow Group 12B at the point of attachment, transitioning to Red Group 51D, and finally near Red-Purple 66A towards the apex. Under surface: Yellow Group 4C at the point of attachment blending to Red-Purple Group 59D towards the apex. Fragrance: none noticeable. Petal number: commonly 5 under normal growing conditions. Petal length: commonly approximately 4.5 cm on average. Petal width: commonly approximately 4.8 cm on average. Petal shape: broadly obcordate. Petal margin: entire. Petal apex: obcordate. Petal base: cuneate Petal drop: good, the petals commonly detach cleanly and freely drop upon full maturity. Stamen number approximately 82 on average. Anthers: commonly near Greyed-Yellow Group 162A in coloration. Filaments: approximately 8 mm in length, and the coloration commonly is near Yellow-Orange Group 14B. Pollen: commonly present in a moderate quantity, and near Greyed-Yellow Group 162A in coloration. Pistils: separate and free, and commonly number approximately 15 on average. Styles: commonly covered with short pubescence, commonly approximately 3 mm in length, less than 1 mm in diameter, and near Yellow-Orange 19D in coloration. Stigma: commonly approximately 1 mm in diameter, and near Yellow Group 11A in coloration. Receptacle: commonly ovoid in shape, approximately 7 mm in diameter, smooth in texture, near Yellow-Green Group 144D overlaid with Red-Purple Group 60A in coloration, and with achenes commonly being present on the bottom and wall. Hips: commonly formed in a moderate quantity, generally ovoid, approximately 1.5 cm in diameter, and near Orange Group 25A in coloration. Seeds: commonly approximately 6 mm in length, approximately 3 mm in diameter, and near Greyed-Yellow Group 161A in coloration.

Development:

*Vegetation*.—Vigorous.

*Blossoming*.—Abundant and commonly reflushes into late summer.

*Resistance to diseases*.—Excellent, particularly with respect to black spot, rust and mildews.

Plants of the 'Radsouththree' variety have not been observed under all possible environmental conditions to date. Accordingly, it is possible that the phenotypic expression may vary somewhat with changes in light intensity and duration, cultural practices, and other environmental conditions.

I claim:

1. A new and distinct Landscape Shrub rose plant characterized by the following combination of characteristics:

(a) abundantly forms attractive single dark pink blossoms having yellow centers that finish to a coral red coloration, (b) exhibits a compact and bushy growth habit, (c) forms vigorous vegetation, (d) forms attractive dark green foliage that is glossy on the upper surface and contrasts well with the blossom coloration, (e) exhibits excellent disease resistance particularly with respect to black spot, rust, and mildews, and (f) is well suited for growing as attractive ornamentation in the landscape;

substantially as herein shown and described.

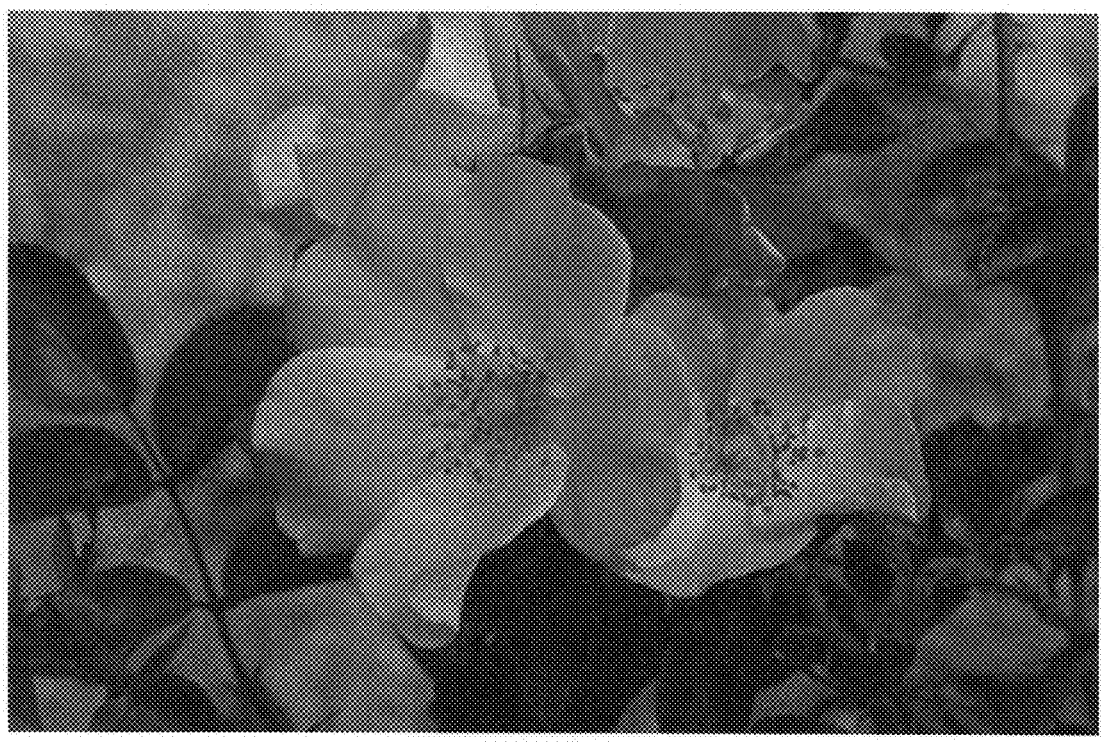

* * * * *